(12) United States Patent
Fu

(10) Patent No.: US 10,966,664 B2
(45) Date of Patent: Apr. 6, 2021

(54) DYNAMICALLY CALIBRATED BLOOD PRESSURE REFERENCE VALUE ELECTRONIC SPHYGMOMANOMETER

(71) Applicant: Kayden Beibei Fu, Rockville, MD (US)

(72) Inventor: Kayden Beibei Fu, Rockville, MD (US)

( * ) Notice: Subject to any disclaimer, the term of this patent is extended or adjusted under 35 U.S.C. 154(b) by 120 days.

(21) Appl. No.: 16/032,047

(22) Filed: Jul. 10, 2018

(65) Prior Publication Data
US 2019/0000395 A1    Jan. 3, 2019

(51) Int. Cl.
*A61B 5/00*    (2006.01)
*A61B 5/022*    (2006.01)
*A61B 5/021*    (2006.01)

(52) U.S. Cl.
CPC ........... *A61B 5/7221* (2013.01); *A61B 5/022* (2013.01); *A61B 5/02141* (2013.01); *A61B 5/02208* (2013.01); *A61B 5/7246* (2013.01); *A61B 5/742* (2013.01); *A61B 5/746* (2013.01); *A61B 5/7475* (2013.01); *A61B 2560/0223* (2013.01); *A61B 2560/0238* (2013.01)

(58) Field of Classification Search
CPC ..... A61B 5/7275; A61B 5/7276; A61B 5/746; A61B 5/7282; A61B 5/021; A61B 5/022; A61B 5/02208; A61B 5/7221; A61B 5/02141; A61B 5/7246; A61B 5/742; A61B 5/7475; A61B 2560/0223; A61B 2560/0238

See application file for complete search history.

(56) References Cited

U.S. PATENT DOCUMENTS

2018/0085011 A1\*  3/2018  Ma ................. A61B 5/7203
2019/0095957 A1\*  3/2019  Ibarria ............ A61B 5/7271
2019/0313982 A1\* 10/2019  Brigham .......... A61B 5/021

\* cited by examiner

*Primary Examiner* — Steven O Douglas
(74) *Attorney, Agent, or Firm* — Syncoda LLC; Feng Ma

(57) ABSTRACT

The invention is a type of electronic sphygmomanometer with dynamically calibrated blood pressure reference value, which is determined based on the objective condition of human blood pressure fluctuation influenced by various factors such as age, date and time of measurement, and establishes age/blood pressure reference value, date/blood pressure reference value and time/blood pressure reference. The value database, or through mathematical operations, obtains the real-time standard blood pressure reference value under the specific conditions of the subject's age, test date, and test time, and calibrates it as a benchmark for judging the abnormality state of the real-time blood pressure measurement value. This improves the ability of the sphygmomanometer in producing an accurate judgement of the subject's blood pressure, and reduces the margin of error for false positive tests or false negative tests.

4 Claims, 6 Drawing Sheets

--Prior Art--

| Age \ Blood pressure | Systolic pressure (mmHg) | Diastolic pressure (mmHg) |
|---|---|---|
| 16-20 | 115 | 73 |
| 21-25 | 115 | 73 |
| 26-30 | 115 | 75 |
| 31-35 | 117 | 76 |
| 36-40 | 120 | 80 |
| 41-45 | 124 | 81 |
| 46-50 | 128 | 82 |
| 51-55 | 134 | 84 |
| 56-60 | 137 | 84 |
| 61-65 | 148 | 86 |

FIG 4

DYNAMICALLY CALIBRATED BLOOD PRESSURE REFERENCE VALUE ELECTRONIC SPHYGMOMANOMETER

CROSS-REFERENCE TO RELATED APPLICATIONS (Not Applicable)

STATEMENT REGARDING FEDERALLY SPONSORED RESEARCH OR DEVELOPMENT (Not Applicable)

REFERENCE TO SEQUENCE LISTING, A TABLE, OR A COMPUTER PROGRAM LISTING COMPACT DISC (Not Applicable)

BACKGROUND

Cardiovascular disease is one of the three most common diseases among humans, alongside diabetes and cancer. Abnormal blood pressure is the most dangerous factor of cardiovascular diseases. The characteristics of chronic diseases with abnormal blood pressure are obvious, and many patients suffer from these diseases. Daily blood pressure monitoring is an important method to prevent stroke and heart disease. There is a huge demand for non-medical (self-testing by patients and family members outside the doctor) blood pressure monitoring, placing new requirements on the convenience and the accuracy of abnormal blood pressure assessments.

The electronic sphygmomanometer technology is developed and widely used. The mainstream products are available in both arm and wrist styles. They have real-time blood pressure data (systolic/diastolic pressure) measurement display, abnormal blood pressure warning information, heart rate display, and other major functions (such as date, time, battery display, and other ancillary information display functions). The reference value of the abnormal blood pressure data of the existing electronic sphygmomanometers is a fixed value (such as 120/80, www.cdc.gov). The real-time measured blood pressure value is compared with the fixed blood pressure reference value to determine whether the real-time measured blood pressure value is abnormal and to provide warning messages about blood pressure status (sound, light, icons, and etc.).

Since the human blood pressure is affected by age, measurement date and time of day, the above-mentioned single factors and multiple factors can all lead to blood pressure fluctuations. Many false judgements of blood pressure status can occur when these factors are neglected and the real-time measured numerical value is compared to a fixed standard value. Thus, the existing electronic sphygmomanometers have obvious deficiencies or defects.

The available technical information (FIG. 4, www.360doc.com) shows that the standard reference value of systolic blood pressure for males between the ages of 61 and 65 is about 129% of the standard systolic blood pressure reference value for males aged 16 to 20 years, with a fluctuation of 33 mmHg and a standard diastolic blood pressure fluctuation of 13 mmHg between these age groups.

The date (month) has a more prominent effect on blood pressure fluctuations. The reference values for standard systolic blood pressure are about 140 mmHg in April and December, the reference value for standard systolic blood pressure in September is about 100 mmHg which shows a fluctuation amplitude of about 40 mmHg. Likewise, the standard diastolic blood pressure fluctuation between these months is about 30 mmHg (as shown in FIG. 5, www.sohu.com).

At the same time, the values of blood pressure fluctuation at different times of the day (24 hours) are also obvious. The standard systolic blood pressure peak at 8:00 am and 4:00 am is 140 mmHg while the peak of the standard diastolic blood pressure at these times is 100 mmHg. In comparison, the peak standard systolic pressure is about 95 mmHg at 2 am, and the peak standard diastolic pressure is about 60 mmHg at the same time (as shown in FIG. 6, www.sohu.com). The fluctuation amplitudes are 45 mmHg and 35 mmHg, respectively.

The above data show that in current sphygmomanometers, only a fixed value of the blood pressure reference value (such as 120/80 mmHg) is used as a benchmark for the real-time measured blood pressure value, making it difficult to correctly judge whether the real-time blood pressure is abnormal or not, leading to errors in the abnormal blood pressure warning information of the existing electronic sphygmomanometer. Because one fixed blood pressure reference value neglects age, date and time, the possibility of a false judgment by patients and their family members is very high. Only doctors can correctly judge the status of the real-time measured blood pressure data of the measured subjects according to their respective information. This deficiency or defect in the sphygmomanometers may cause it to be a harmful instrument to patients and other users by committing false positive or false negative errors.

BRIEF SUMMARY OF THE INVENTION

The invention proposed is a type of electronic sphygmomanometer that dynamically calibrates real-time blood pressure standards. The dynamically calibrated blood pressure reference value electronic sphygmomanometer according to the invention can dynamically calibrate the real-time blood pressure reference value of the measured subject according to the age of the measured object, date and time of measurement. Furthermore it analyzes the deviation between the real-time measured blood pressure and the real-time blood pressure reference value to accurately assess blood pressure status of the measured subject. The comparison to dynamically calibrated reference values makes it possible to significantly increase the accuracy of the blood pressure abnormality information of the electronic sphygmomanometer and, to a certain extent, make it easier for the user or family to analyze or monitor blood pressure.

The electronic sphygmomanometer's blood pressure reference standards value is real-time dynamically calibrated, including blood pressure data acquisition, a microprocessor MCU and a monitor. The real-time blood pressure reference value ($BP_{reference}$) is dynamically calibrated by age, date (month) and measurement time, that is, $BP_{reference}$=blood pressure reference standard value ($BP_{stand}$)+blood pressure fluctuation value ($\Delta BP$), where $\Delta BP$ includes age blood pressure fluctuation value ($BP_{age}$), date blood pressure fluctuation value ($BP_{date}$), and time blood pressure fluctuation value ($BP_{time}$). In other words, $BP_{reference}=BP_{stand}+\Delta BP_{age}+\Delta BP_{date}+\Delta BP_{time}$. The MCU is configured to analyze the deviation between real-time blood pressure and the real-time blood pressure reference value in order to describe the abnormality of the real-time blood pressure status; The real-time blood pressure reference value $BP_{reference}$ value is determined by the MCU through searching the age/blood pressure reference value database, the date/blood pressure reference value database and the measurement time/blood pressure reference database to obtain the age blood pressure fluctuation value ($BP_{age}$), date blood pressure fluctuation value ($BP_{date}$), and time blood pressure fluctuation value ($BP_{time}$), according to the formula: $BP_{reference}=BP_{stand}+\Delta BP$ or $BP_{reference}=BP_{stand}+\Delta BP_{age}+\Delta BP_{date}+\Delta BP_{time}$. The display shows the standard real-time blood pressure reference value $BP_{reference}$, measured blood pressure value $BP_{real-time}$, and an analysis of the blood pressure status, or a warning of abnormalities.

The blood pressure reference value dynamically calibrated electronic sphygmomanometer is characterized in that:
  a. the age/blood pressure reference value database is a data collection of the age (group) of the measured object and the set of corresponding blood pressure reference values ($BP_{reference}$) according to age (group).
  b. The date/blood pressure reference value database is a data collection of the date of measurement (month) and the set of corresponding blood pressure reference values ($BP_{reference}$) according to the date (or month).
  c. The time/blood pressure reference value database is a data collection of the time of measurement and the corresponding blood pressure reference values ($BP_{reference}$) according to the time.
  d. Databases are stored in ROM—S102 (but not limited to ROM).

The blood pressure reference value dynamically calibrated electronic sphygmomanometer is also characterized in that: the input of age data of the measured object is carried out by human-computer interaction (HCI), including a touch screen, key input and voice input, etc. The date (month) and measurement time data is provided by an MCU clock unit or an independent clock unit, or provided by an electronic timing system such as a Wi-Fi signal timing.

The dynamically calibrated electronic sphygmomanometer contains an analysis of the real-time blood pressure status, wherein the real-time measured blood pressure value is displayed in a single-side arrow-shaped graphic frame, and the arrow points to the middle position of the blood pressure warning bar.

The main display contents of the dynamic calibrated blood pressure reference value electronic sphygmomanometer display interface include: (see FIG. 2.)
  1. Age data display of the measured object,
  2. Date, time display,
  3. Real-time blood pressure reference value (systolic/diastolic pressure) data display,
  4. Real-time measured blood pressure (systolic/diastolic) data display,
  5. Abnormal blood pressure information sound and light tips, battery power display.

BRIEF DESCRIPTION OF DRAWINGS

FIG. 4 is a table of age/blood pressure (systolic/diastolic) reference value data.

DETAILED DESCRIPTION OF THE INVENTION

Figure 1:
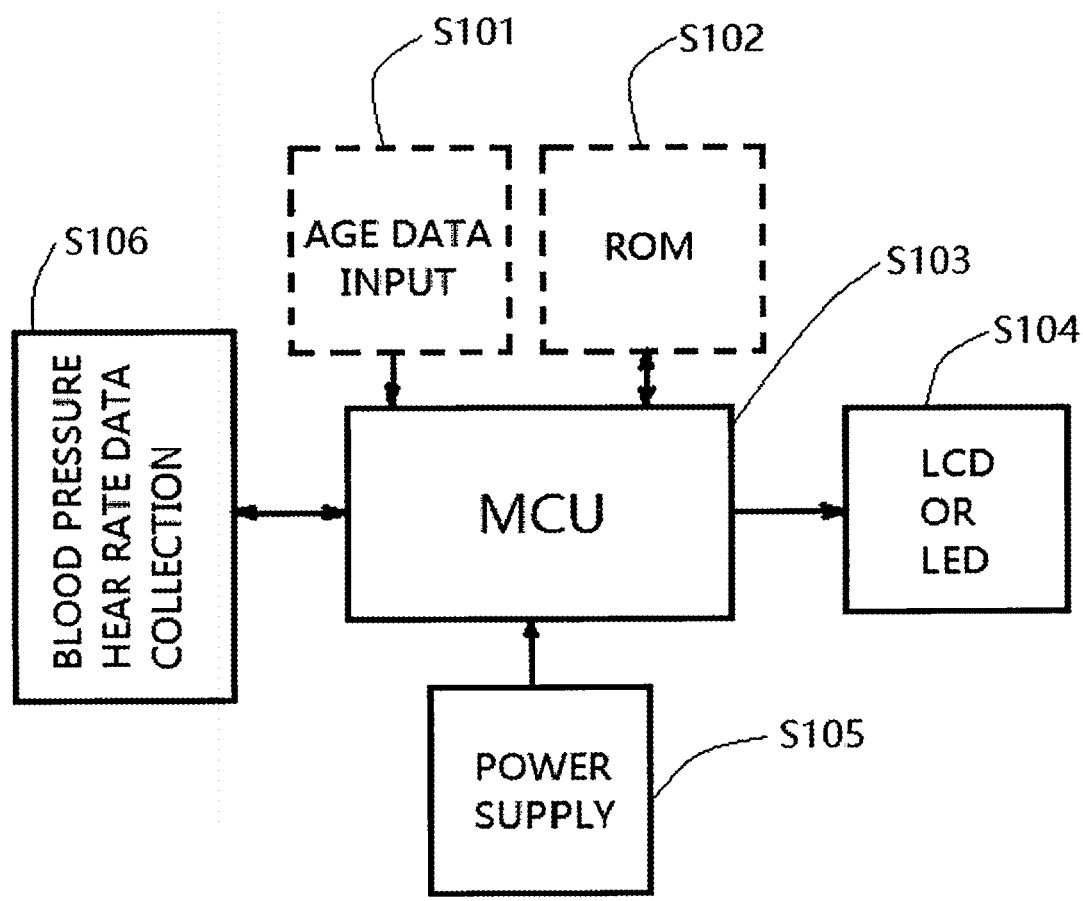
FIG. 1 is a schematic block diagram of a dynamically calibrated electronic sphygmomanometer with a blood pressure reference value according to the present invention.

The specific embodiments of the invention will be described in detail below with reference to the accompanying drawings. As shown in FIG. 1, the present invention is composed of six parts, specifically including a blood pressure (heart rate) data acquisition unit—S106, a measured subject information data input unit—S101, a database (age/blood pressure reference value, date/blood pressure reference value, time/blood pressure reference value) storage unit—S102, an microprocessor MCU—S103, a display—S104 and a power supply—S105. The solid line represents the frame part of existing electronic sphygmomanometers. The information data input unit—S101 and data storage unit—S102 of the measured object are shown by the dashed line frame and are contents of the invention new to existing sphygmomanometers.

Figure 2:
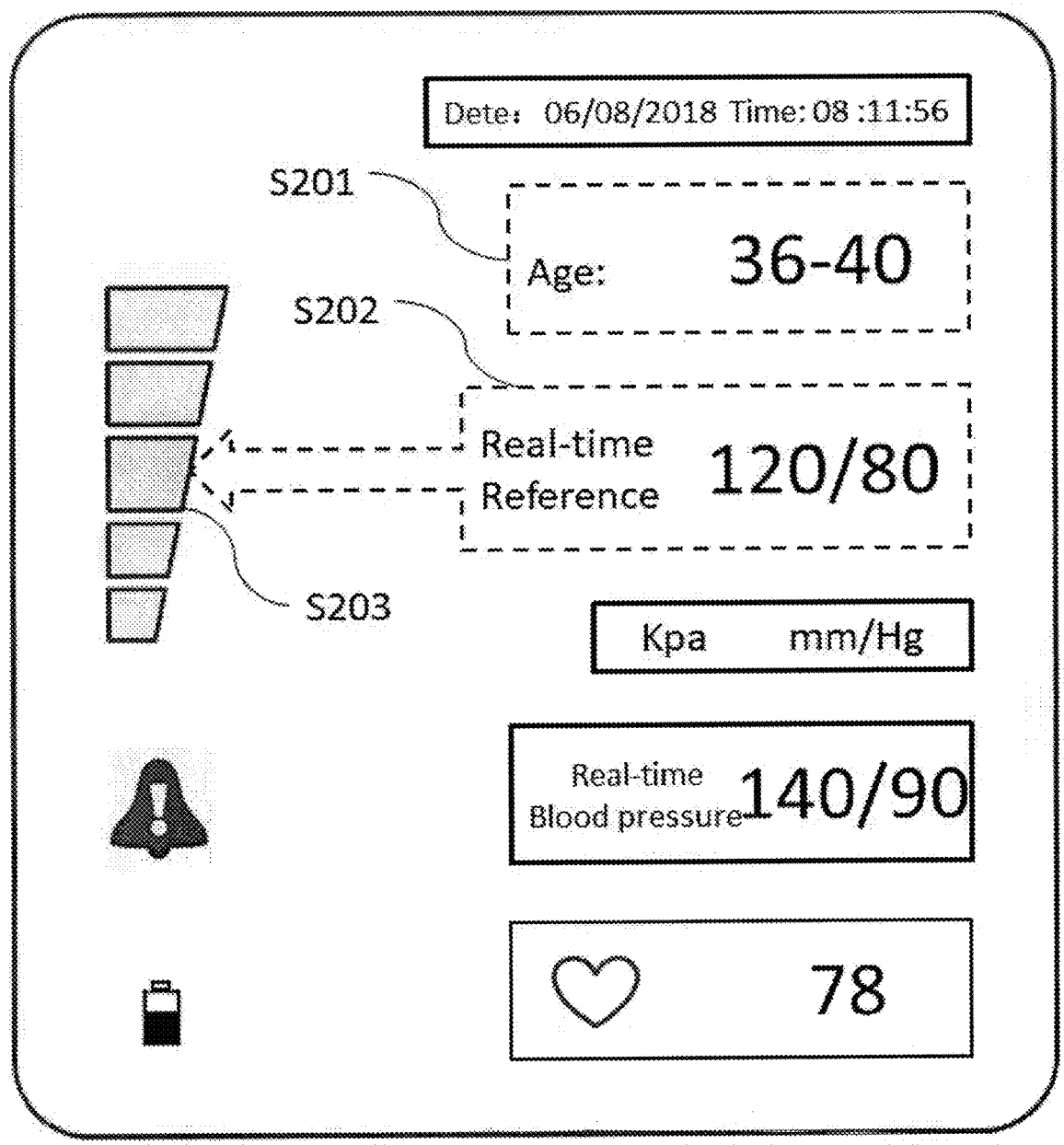
FIG. 2 is a schematic diagram of a display interface of a blood pressure reference value dynamic calibration electronic blood pressure monitor according to the present invention.

FIG. 2 is a schematic diagram of a display unit according to the invention. The dashed line frame portion—S201, S202—is a content of the proposed invention that is new to existing sphygmomanometers, which are the real-time blood pressure reference value data display and the age data display. Age data can be input through a touch screen or a key input method (conventional technology design, not shown on FIG. 2) to adjust the age data to match the age of the measured subject. Then the MCU can use the displayed data as the age data of the measured subject.

The real-time blood pressure reference value data is displayed in a single-sided arrow-shaped graphic frame. The arrow points to the middle position of the blood pressure warning bar, and the image intuitively indicates the meaning of the blood pressure reference value.

The clock display (circuit) is a standard configuration of an existing electronic sphygmomanometer, providing date (day, month, year) and time data, including a MCU-driven clock unit, an independent clock unit independent of the MCU, and a wireless (eg WIFI) timing clock unit. The date and measurement time data of this sphygmomanometer invention can be obtained through the above three methods. When the blood pressure monitor (sphygmomanometer) is powered on, the MCU obtains the date and time data to dynamically calibrate the blood pressure reference value with the date and measurement time data.

Figure 3:
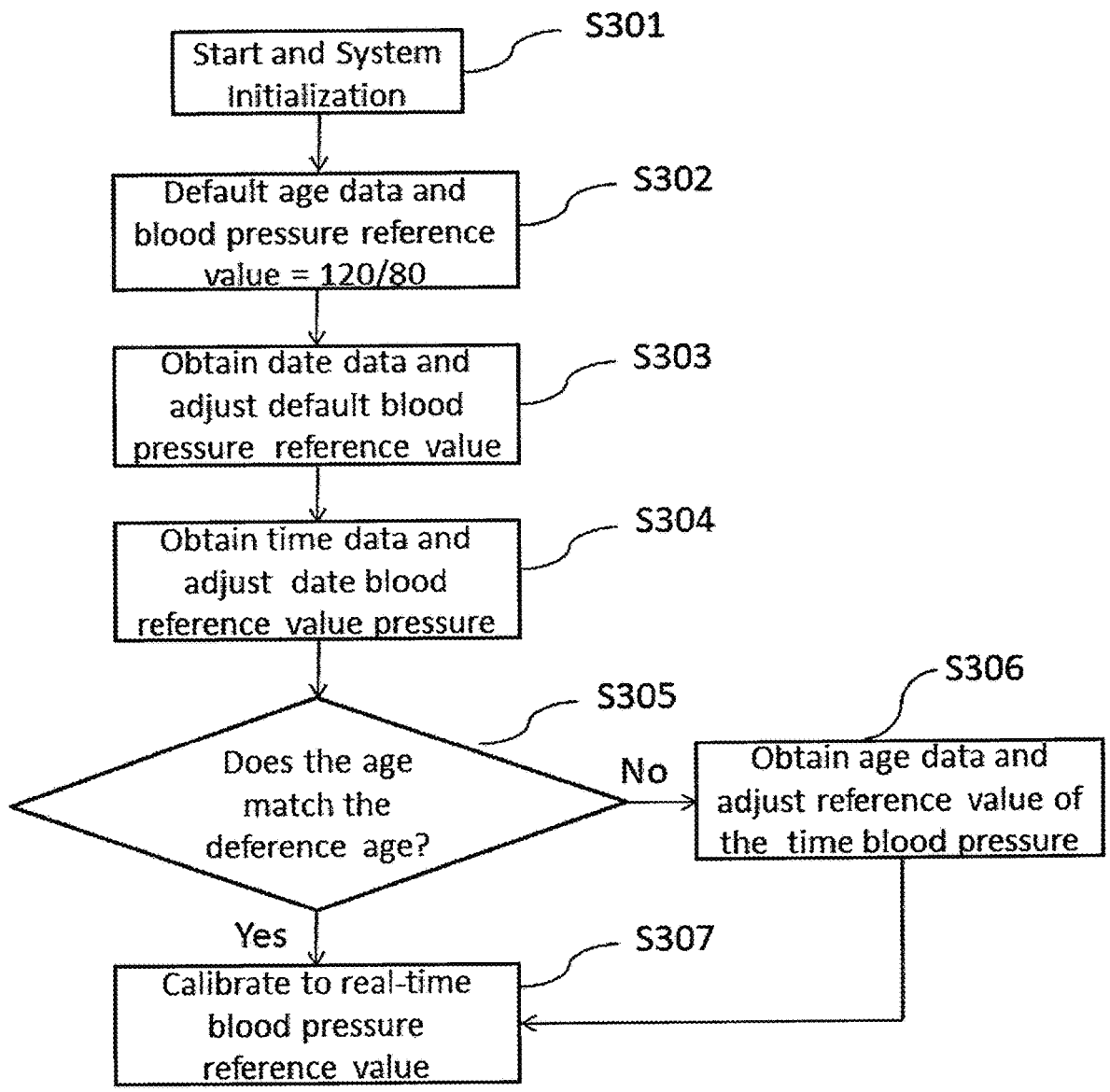
FIG. 3 is a flow chart of the dynamic calibration procedure of the blood pressure reference value.
Figure 5:
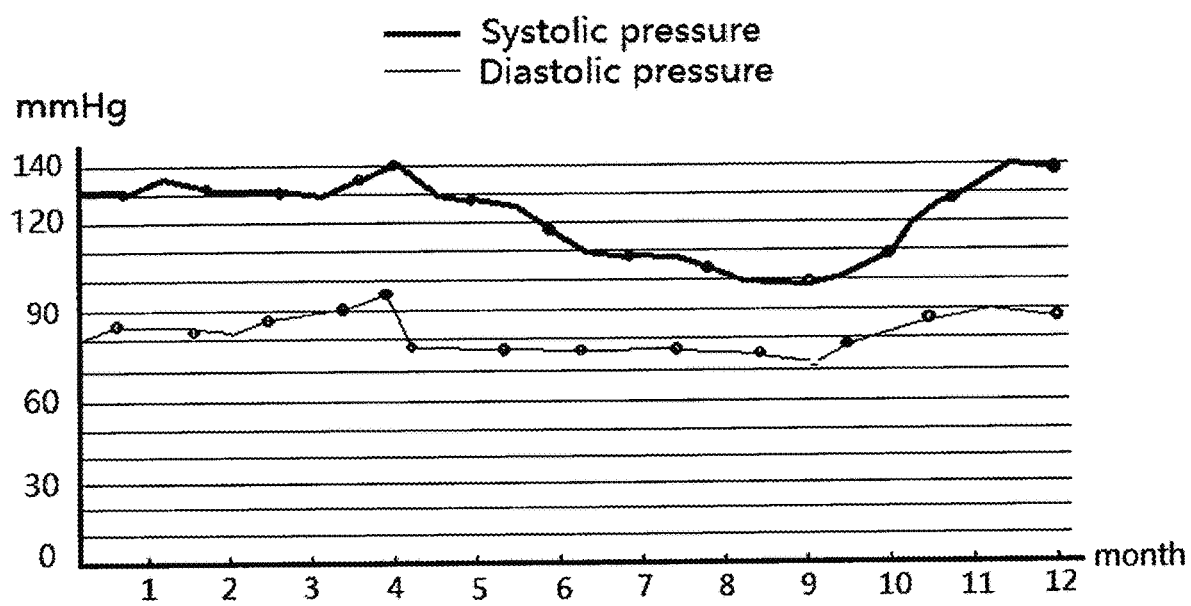
FIG. 5 is a graph of date/blood pressure (systolic/diastolic pressure) fluctuations.
Figure 6:
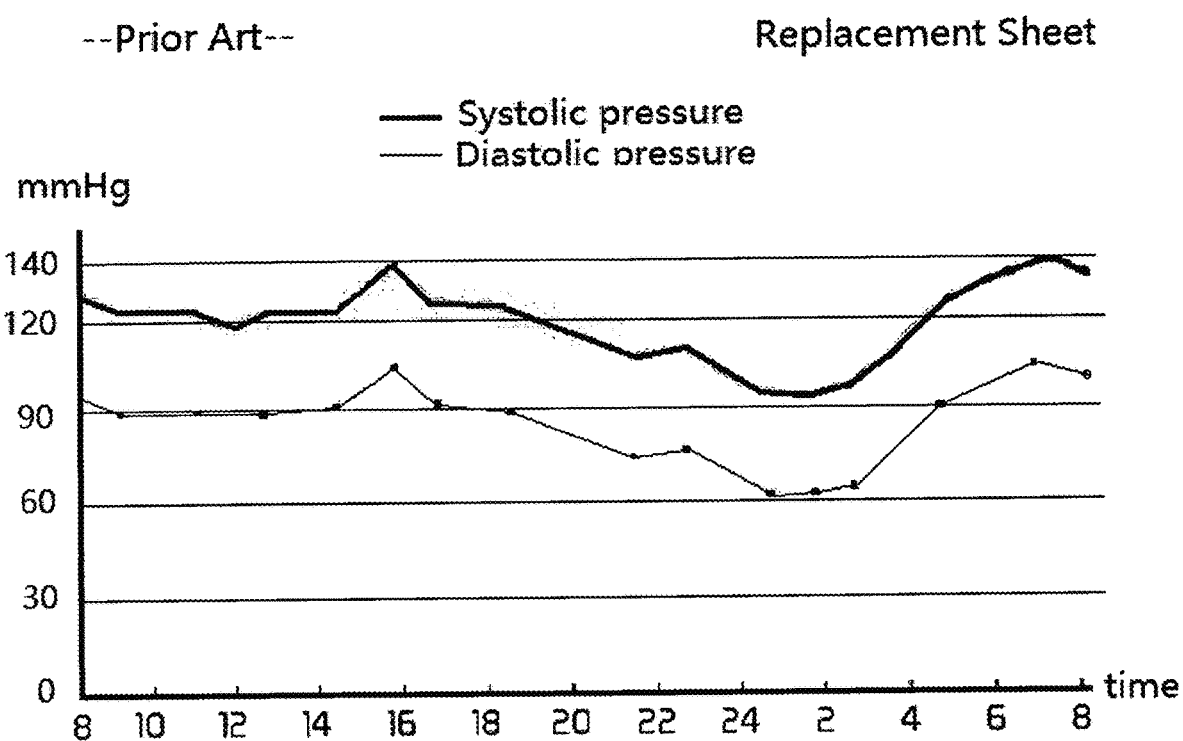
FIG. 6 is a graph of time/blood pressure (systolic/diastolic pressure) fluctuations.

FIG. 3 is a flowchart of the dynamic calibration procedure of the blood pressure reference value of this invention. The program flow is as follows:
  1. After the power of the sphygmomanometer is turned on, the system (MCU) is initialized—step S301;
  2. The default age data is the median age (36-40 years), the standard blood pressure reference value is 120/80, —step S302;
  3. Collect the date data and adjust the blood pressure reference value, —step S303;
  4. Collect time data and adjust the blood pressure reference value, —step S304;
  5. Does the age match the default age—step S305? If not, the age data is used to modify the blood pressure reference value—step S306. If yes, maintain the age data as the default value, and maintain the blood pressure reference value as corrected by time data—step S307. That is, when the condition data of the measured age, measurement date, and measurement time are obtained, the system (MCU) dynamically calibrates the real-time blood pressure reference value data of the measured subject through database search and conventional mathematical operations.

In addition to the real-time standard blood pressure reference data through three conditions of age, date and time dynamic calibration procedure, the real-time blood pressure measurement procedure of the electronic sphygmomanometer of the present invention is the same as the existing electronic sphygmomanometers. After the real-time blood pressure measurement data is generated, the MCU compares and calculates the real-time blood pressure data with the real-time standard blood pressure reference value data to determine the (ab)normality state of the measured subject, and drives the display to display the real-time blood pressure data and blood pressure abnormality information of the measured subject.

The invention claimed is:

1. An electronic sphygmomanometer comprising:
    a blood pressure data acquisition component,
    a microprocessor (MCU), and
    a display, wherein:
        the electronic sphygmomanometer is configured with dynamically calibrated blood pressure reference values;
        a real-time blood pressure reference value ($BP_{reference}$) is dynamically calibrated by age, date and measurement time based on $BP_{reference}$=blood pressure reference standard value ($BP_{stand}$)+blood pressure fluctuation value ($\Delta BP$), where $\Delta BP$ includes age blood pressure fluctuation value ($\Delta BP_{age}$), date blood pressure fluctuation value ($\Delta BP_{date}$), and time blood pressure fluctuation value ($\Delta BP_{time}$), and the real-time blood pressure reference value is calculated based on $BP_{reference}=BP_{stand}+\Delta BP_{age}+\Delta BP_{date}+\Delta BP_{time}$;

the MCU is configured to analyze a deviation between a real-time blood pressure and the real-time standard blood pressure reference value in order to describe an abnormality status of the real-time blood pressure;
    b. the real-time blood pressure reference value ($BP_{reference}$) is determined by the MCU through a search of a first database having blood pressure reference values in association with ages, a second database having blood pressure reference values in association with date, and a third data base having blood pressure reference values in association with measurement time based on:

$BP_{reference}=BP_{stand}+\Delta BP=$ $BP_{reference}=BP_{stand}+\Delta BP_{age}+\Delta BP_{date}+\Delta BP_{time}$, where $\Delta BP=\Delta BP_{age}+\Delta BP_{date}+\Delta BP_{time}$;
        the display is configured to display:
        the real-time blood pressure reference value,
        the real-time blood pressure; and
        an analysis of the real-time blood pressure including a warning of the abnormality status.

2. The electronic sphygmomanometer of claim 1, wherein:
    the first database is a data collection of the ages of a population group and corresponding blood pressure reference values ($BP_{reference}$);
    the second database is a data collection of the date of measurement and corresponding blood pressure reference values ($BP_{reference}$);
    the third database is a data collection of the time of measurement and corresponding blood pressure reference values ($BP_{reference}$);
    the first, second, and third databases are stored in a read-only memory (ROM).

3. The electronic sphygmomanometer of claim 1, wherein:
    the ages of the population group are collected by a human-computer interaction (HCI), including a touch screen, key input and voice input;
    the date of measurement and the time of measurement are provided by an MCU clock unit, an independent clock unit, or a WIFI signal timing.

4. The electronic sphygmomanometer of claim 1, wherein the analysis of the real-time blood pressure includes the real-time blood pressure reference value ($BP_{reference}$) displayed in a single-side arrow-shaped graphic frame with an arrow pointing to a middle position of a blood pressure warning bar.

* * * * *